US012340877B1

(12) United States Patent
Kimball et al.

(10) Patent No.: US 12,340,877 B1
(45) Date of Patent: Jun. 24, 2025

(54) BIOPROCESS EXECUTION WORKFLOW INTERFACES

(71) Applicant: Benchling, Inc., San Francisco, CA (US)

(72) Inventors: Aaron Kimball, San Francisco, CA (US); Aaron Valade, San Francisco, CA (US); Christian Arca, Portland, OR (US); Dane Colin Pieri, Winchester, MA (US); James Pycock, Moraga, CA (US); Rohan Bhargava, San Ramon, CA (US); Vic Woeltjen, Anaheim, CA (US)

(73) Assignee: Benchling, Inc., San Francisco, CA (US)

( * ) Notice: Subject to any disclaimer, the term of this patent is extended or adjusted under 35 U.S.C. 154(b) by 0 days.

(21) Appl. No.: 18/807,846

(22) Filed: Aug. 16, 2024

(51) Int. Cl.
  *G06Q 10/0631* (2023.01)
  *G16C 20/10* (2019.01)
  *G16C 20/90* (2019.01)

(52) U.S. Cl.
  CPC ....... *G16C 20/90* (2019.02); *G06Q 10/06316* (2013.01); *G16C 20/10* (2019.02)

(58) Field of Classification Search
  None
  See application file for complete search history.

(56) References Cited

U.S. PATENT DOCUMENTS 6,041,263 A   3/2000  Boston et al.
7,392,107 B2  6/2008  Popp
              (Continued)

FOREIGN PATENT DOCUMENTS

CN    113721567       11/2021
EP      3122892 B1  *  8/2021  ............. G16B 50/00
              (Continued)

OTHER PUBLICATIONS

Patrick "Systematizing scientific laboratory work by a workflow and template for electronic laboratory notebooks", Dec. 2020, Education for Chemical Engineers, pp. 42-53 (Year: 2020).*

(Continued)

*Primary Examiner* — Romain Jeanty
(74) *Attorney, Agent, or Firm* — Fish & Richardson P.C.

(57) ABSTRACT

Methods, systems, and apparatus, including computer programs encoded on a computer storage medium, for automatic or semi-automatic bioprocess design, execution, and analysis. In one aspect, a system comprises receiving a request to execute a sequence of unit operations specified by a recipe representing a bioprocess, wherein each unit operation defines one or more steps to be performed, generating, for each step of each unit operation, a worksheet representing laboratory effects of performing the step and having a worksheet interface for displaying bioprocess data and receiving execution data, including initializing, for each worksheet, a corresponding electronic laboratory notebook object in an underlying electronic laboratory notebook subsystem, receiving execution data entered into the worksheet (Continued)

interface for a particular step of a first unit operation, and updating, in the electronic laboratory notebook subsystem, the corresponding electronic laboratory notebook object using the execution data.

19 Claims, 10 Drawing Sheets

(56) References Cited

U.S. PATENT DOCUMENTS

| | | | |
|---|---|---|---|
| 8,738,190 B2 | 5/2014 | Pai et al. | |
| 9,226,875 B2* | 1/2016 | Foshee | A61J 1/2089 |
| 10,088,837 B1 | 10/2018 | Strain et al. | |
| 10,656,628 B2 | 5/2020 | Feiten et al. | |
| 10,671,035 B2 | 6/2020 | Feiten et al. | |
| 11,079,896 B2* | 8/2021 | Sciola | G06F 30/20 |
| 11,086,302 B2 | 8/2021 | Marruchella et al. | |
| 11,200,031 B2 | 12/2021 | Holbrook et al. | |
| 11,340,876 B2 | 5/2022 | Kim et al. | |
| 2002/0052862 A1 | 5/2002 | Scott et al. | |
| 2005/0149569 A1* | 7/2005 | Hariharan | G16H 10/40 |
| 2007/0050070 A1 | 3/2007 | Strain et al. | |
| 2008/0097623 A1 | 4/2008 | Weatherhead et al. | |
| 2009/0299511 A1 | 12/2009 | Chan et al. | |
| 2013/0144591 A1 | 6/2013 | Khan | |
| 2020/0348662 A1* | 11/2020 | Cella | G05B 19/41865 |
| 2023/0168662 A1 | 6/2023 | Stacey et al. | |

FOREIGN PATENT DOCUMENTS

| | | | | |
|---|---|---|---|---|
| WO | WO-2015148530 A1 * | 10/2015 | | G16B 50/00 |
| WO | WO-2017194473 A1 * | 11/2017 | | G06F 16/10 |
| WO | WO-2021108112 A1 * | 6/2021 | | B01L 1/025 |

OTHER PUBLICATIONS

Roberta "How to pick an electronic laboratory notebook", Aug. 2018, TOOLBOX, pp. 1-8 (Year: 2018).*
U.S. Appl. No. 18/665,429, Pieri et al., filed May 15, 2024.
atlassian.com [online], "All great projects start with Jira," available on or before Aug. 18, 2024, via Internet Archive: Wayback Machine URL<https://web.archive.org/web/20240818005116/https://www.atlassian.com/software/jira>, retrieved on Aug. 22, 2024, URL<https://www.atlassian.com/software/jira>, 11 pages.
camunda.com [online], "What is Business Process Model and Notation (BPMN)?," available on or before Apr. 7, 2023, via Internet Archive: Wayback Machine URL<https://web.archive.org/web/20230407162138/https://camunda.com/bpmn/>, retrieved on Aug. 22, 2024, URL<https://camunda.com/bpmn/s>, 12 pages.
google.com [online], "Build your best ideas together, in Google Docs," available on or before Jan. 13, 2022, via Internet Archive: Wayback Machine URL<https://web.archive.org/web/20220113040742/https://www.google.com/docs/about/>, retrieved on Aug. 22, 2024, URL<https://www.google.com/docs/about/>, 11 pages.
servicenow.com [online], "Put AI to Work With ServiceNow," available on or before Jul. 1, 2024, via Internet Archive: Wayback Machine URL<https://web.archive.org/web/20240701042617/https://www.servicenow.com/>, retrieved on Aug. 22, 2024, URL<https://www.servicenow.com/>, 7 pages.
skylandanalytics.net [online], "Introducing Skyland PIMS®," available on or before Aug. 22, 2024, via Internet Archive: Wayback Machine URL<https://web.archive.org/web/20240822143451/https://skylandanalytics.net/skyland-pims-suite/>, retrieved on Aug. 22, 2024, URL<https://skylandanalytics.net/skyland-pims-suite/>, 7 pages.

* cited by examiner

FIG. 3A

Create study: Process Dev Study    ① Specify metadata    ② Design experiment

Experiment configuration   [+ Add condition ▼]   Variant Specification 360     Conditions 2   Total replicates 2 ⓘ 10s

| | Condition 1 | Condition 2 362 364 |
|---|---|---|
| Condition name | Low Temperature | High Temperature |
| Description | | |
| Number of replicates | 1 | 1 |

Unit operations
Main Fermentation 370

Main Fermentation

Material inputs

| Aa Name | Aa Field | Recipe values | Low Temperature | High Temperature |
|---|---|---|---|---|
| glucose media | Default material | | No change | No change |
| | Amount | | No change | No change |
| anti-foam | Default material | | No change | No change |
| | Amount | | No change | No change |
| antibiotic | Default material | Kan | No change | No change |
| | Amount | | No change | No change |

Default Parameters 375

Parameters

| Aa Name | Recipe setpoint | Low Temperature | High Temperature |
|---|---|---|---|
| stir rpm | 350 | No change | 380 |
| tank temperature | 38 °C | 36 °C | 40 °C |

Variant Parameters 380

⚠ Upon creation, tasks will be generated and you won't be able to edit conditions.

[Cancel]   [Back]   [Proceed to execution]   390

STEPS

| Run | ∨ Prep assay plate | ⊙ ⊙ | Complete step ▶ |

- ○ Prep assay plate
- ○ Shake, incubate, wash
- ○ Add secondary detection antibody
- ○ Shake, incubate, wash
- ○ Add tertiary detection antibody
- ○ Shake, incubate, wash
- ○ Read plate

⎘ ▶ | B | I | U | ⊖ | 𝒮 | ⊘ | </> | A▶ | X₁ | X₂

Instructions

1. Prepare samples at pre-dilution by diluting with water
2. Add assay buffer to plate, then aspirate it
3. Add samples to plate, according to plate map below
4. Dilute to final dilution samples accordingly
5. Add controls to plate, according to plate map below
6. Add Ab-MS to plate, according to plate map below

⊟ Confirm material inputs +

| | Name | ▭ Parent entity | ▭ Planned material | Aa Description | ▭ Material used | Amount used | ⊙ Added At | |
|---|---|---|---|---|---|---|---|---|
| 1 | Assay buffer | | 🗋 Assay Buffer 040224 | | 🗋 Assay Buffer 040224 | | | Submit |

⊞ Confirm parameter setpoints

| | Parameter | Planned Setpoint | Min - Max | Aa Description | Confirm Setpoint | ⊙ Recorded At | Aa Comments | |
|---|---|---|---|---|---|---|---|---|
| 1 | Sample Pre dilution | 1:10 | | | 1:10 | | | Submit |
| 2 | Sample final dilution | 1:10, 1:100 | | | Confirm in plate map | | | |

BIOPROCESS EXECUTION WORKFLOW INTERFACES

BACKGROUND

This specification relates to computing platforms for bioprocess design, execution, and analysis.

Life sciences products, including pharmaceuticals, vaccines, and chemical compounds, are typically developed in a bioprocess development cycle by a process development team using one or more process development facilities. The bioprocess development cycle may involve hundreds or thousands of experiments and trials and can take months or years of development, during which a synthesis or fermentation-based process for making the product, testing its quality and purity, and mixing with other substances to formulate a stable product, is iteratively modified.

The bioprocess development cycle may involve multiple scientists across different process development facilities. After the bioprocess has been developed and vetted, it may be productionized and produced at a production facility. Since the bioprocess development cycle is generally highly manual and can involve many different individuals and collaboration across different facilities, the process is often disorganized and prone to errors. In particular, it can be difficult to monitor and memorialize small deviations from a bioprocess plan during execution of and experimentation on the bioprocess plan.

This specification also relates to user interfaces. User interfaces (UI) can be used to display and interact with data maintained by cloud infrastructure, including servers, networks, and data storage devices. In particular, cloud infrastructure can support the uploading, maintaining, and editing of content on a user device using a UI configured with a data processing system that can store and access the appropriate data.

SUMMARY

This specification describes technologies relating to a cloud-based bioinformatics platform that provides for automatic or semi-automatic bioprocess design, execution, and analysis. To do so, the platform can provide a design tool, execution tool, and bioprocess review tool for designing, executing, and evaluating different versions of a bioprocess. The bioinformatics platform allows for the rapid iteration of different versions of a bioprocess, the maintenance of data relating to the bioprocess design phase, and the finalization of the bioprocess for production.

The bioinformatics system implements a recipe as an underlying data model for a bioprocess. In this specification, a recipe includes one or more unit operations, each parameterized by one or more material inputs, material outputs, steps, equipment, and bioprocess parameters. In this context, a recipe is rich enough and flexible enough that the parameters that were input during the process design phase can be automatically translated to those used in process execution and production.

Each recipe can be configured using the cloud-based bioinformatics platform, and data including results and experimental notes can be added to an electronic laboratory notebook object, e.g., a persistent record for a particular unit operation of a recipe, by way of one or more worksheet interfaces. For example, the electronic laboratory notebook objects can be underlying records stored in a database. Each worksheet interface can provide a worksheet, e.g., a rendered visual presentation of a particular step in the unit operation, that can be modified using the worksheet interface, and the system can automatically generate notebook entry content to populate the worksheet for instructions and data capture for each step of a unit operation. Furthermore, the system can allow for the automatic sharing of execution data between different steps of a particular unit operation and across unit operations using the electronic laboratory notebook objects.

Particular embodiments of the subject matter described in this specification can be implemented so as to realize one or more of the following advantages.

The techniques described in this specification provide for the design, execution, and analysis of a bioprocess. In particular, the recipe design tool, recipe execution tool, and bioprocess review tool facilitate the creation of a bioprocess as a modular workflow that is easily modifiable and recordable.

In contrast to form-based step-by-step execution mechanisms which require the filling out of precise predetermined fields, the bioinformatics platform allows for the flexibility to enter in new information and new types of data in a different format than is provided for in the initial bioprocess configuration via the worksheet interface. The worksheet interface both provides the necessary structure to support the configured bioprocess, e.g., the worksheet including the steps of the particular unit operation being executed, instructions, and material input, material output, and result input for capturing measurements or scientific results from the unit operation, etc., while supporting the modification of any component in real-time execution. This is in contrast to most workflow engines where each step is typically represented by filling out a form with whatever structured data is required by the initial bioprocess configuration.

Moreover, the system allows for certain kinds of information commonly present in lab data, e.g., rich-formatted text, photos of lab setup, attachments like excel spreadsheets, etc. to be integrated directly into the step to which they pertain, e.g., by way of the worksheet interface as a modification. Rather than attaching an element to a form, the system can embed the rich-formatted text, photos, or spreadsheets directly in the worksheet by way of the worksheet interface.

Additionally, the system of this specification can generate and maintain analysis-ready electronic laboratory notebook objects tailored to the needs of a process development scientist. The electronic laboratory notebook objects can be generated for each unit operation of a bioprocess, can be maintained, and can be viewed and updated by the same or another user. In particular, the electronic laboratory notebook objects can facilitate experiment planning for multiple rounds of experiments, e.g., that deviate from a primary protocol in small and controlled ways, guide lab operations staff through the execution of the wet lab activities required in service of those successive rounds of experiments, collect data from those experiments, and provide a verifiable persistent record of the various steps, e.g., for compliance.

For example, the system can allow for the organization of multiple iterations of a step within a single experiment, including any modifications made at execution time, through multiple worksheets and multiple corresponding electronic laboratory notebook objects, and can memorialize results produced at different times as part of different rounds of performing the same experiment. As another example, the system can allow for the varying of default values of bioprocess parameters encoded in the workflow in a design-of-experiment setting to generate multiple copies of a worksheet for different experimental conditions. Since each worksheet has a corresponding electronic laboratory notebook object, the system can maintain a clear record of the experiment and associate the experiment with a given bioprocess.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 3A and 3B illustrate example user interface displays for designing a study including multiple executions of a recipe.

FIGS. 4A, 4B, and 4C illustrate example user interface displays for corresponding worksheets initialized from the recipe.

Like reference numbers and designations in the various drawings indicate like elements.

DETAILED DESCRIPTION

Figure 1:
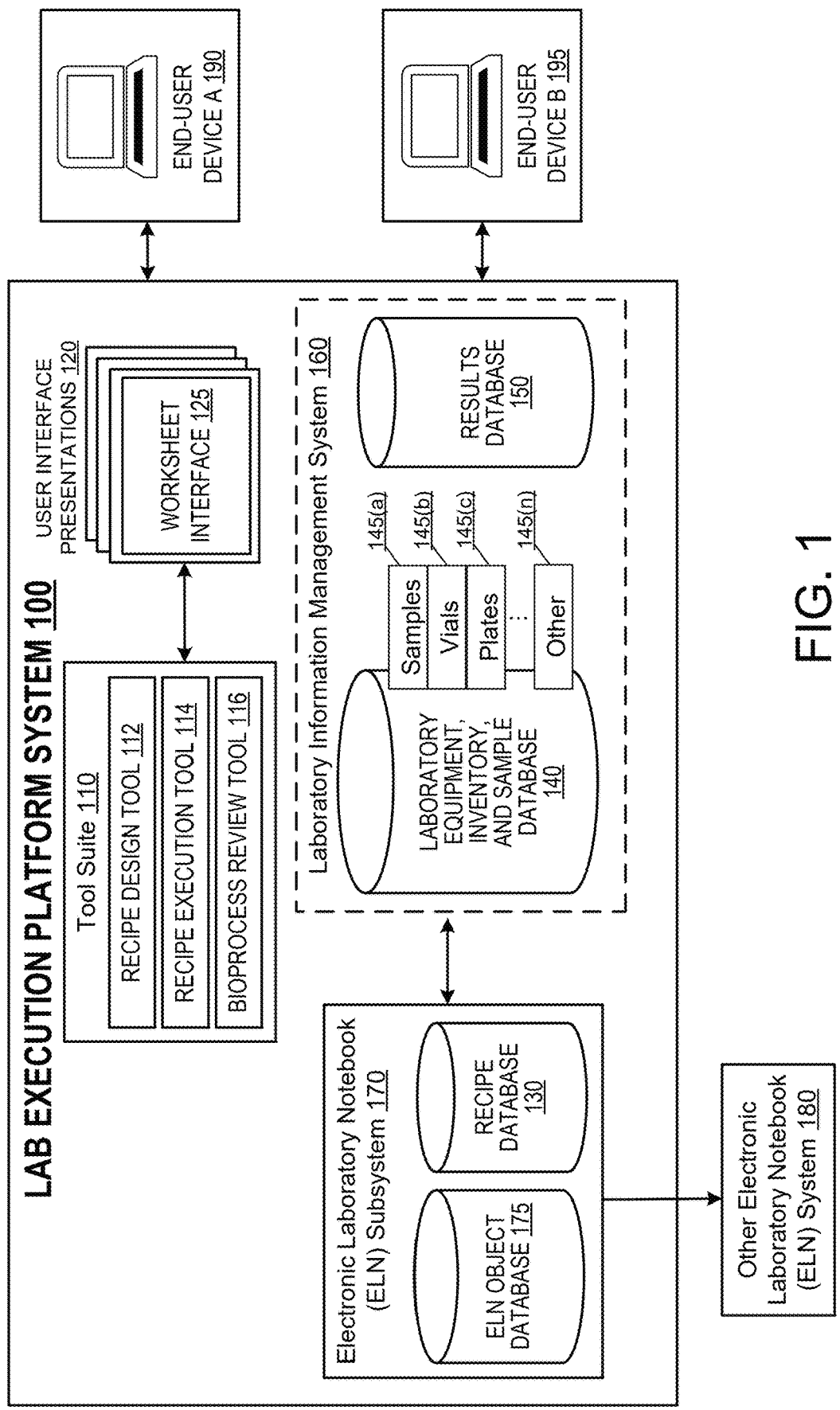
FIG. 1 is a system diagram of an example lab execution platform system.

FIG. 1 shows an example lab execution platform system 100. The lab execution platform system 100 is an example of a system implemented as computer programs on one or more computers in one or more locations in which the systems, components, and techniques described below are implemented.

The lab execution platform system 100 can automate the bioprocess design cycle. In particular, the system 100 allows for the rapid iteration of different versions of a bioprocess, the maintenance of data relating to the bioprocess design phase, and the finalization of the bioprocess for production. The system 100 can also employ an electronic laboratory notebook object that is compatible with other systems in order to capture a record of what happened as the bioprocess was being executed or experimented on and provide for the automated organization of the contributions of many different individuals and facilities to a bioprocess design. The system 100 can provide one or more tools to any appropriate computing devices at an appropriate bioprocess facility, e.g., the end-user device A 190 and the end-user device B 195, for bioprocess design, execution, and analysis. For example, the appropriate bioprocess facility can be a process development facility, e.g., a lab for designing processes for drug synthesis, gene editing, or any other appropriate life sciences process, or production facility, e.g., for producing a drug following a bioprocess designed in a process development facility. As an example, the end-user devices 190, 195 can be a tablet, a laptop, an internet of things (IoT) device, a mobile phone, a desktop, etc.

The system 100 can manage a tool suite 110 that includes a recipe design tool 112, recipe execution tool 114, and a bioprocess review tool 116. The tools 112, 114, 116 can be implemented as a cloud-based application that provides a user interface for users, e.g., users of the end-user device A 190 and end-user device B 195. Alternatively or in addition, some or all of the process development tool 150 can be installed locally on the end-user devices 190, 195.

The system 100 can provide the tools 112, 114, and 116 to a user by way of one or more user interface presentations 120, e.g., by establishing a network connection with the end-user devices 190 and 195, for data transfer and capture by way of the user interface presentations 120. For example, the network can be a cloud-based network, the internet, or a local network.

In particular, the system 100 can leverage the power and flexibility of a recipe data model, as described in U.S. patent application Ser. No. 18/665,429, which is herein incorporated by reference, to allow for organized bioprocess management. In this specification a recipe is a data model that comprehensively represents a bioprocess. In this case, a recipe includes one or more unit operations, each parameterized by one or more inputs, outputs, steps, and equipment, that can be executed in order to perform the bioprocess. Such bioprocesses often involve making, purifying, or testing materials in a laboratory.

The system 100 can provide a recipe design tool 112 for a user to generate a recipe as a bioprocess template. In this context, generating a bioprocess template refers to designing a sequence of unit operations that can be performed as part of an experiment.

Each unit operation is data that represents a subset of a process that transforms a material input to a material output. A unit operation can represent a physical transformation, a chemical transformation, or both. In general, the parameters of a unit operation can be modified without impacting other unit operations in a recipe. A recipe typically includes at least one sequence of unit operations. A recipe can however include multiple sequences of unit operations or any appropriate directed graph of unit operations.

More specifically, each unit operation is a portion of a recipe that represents the transformation of a material input to a material output through a series of discrete steps that a user can specify using a user interface 120. An example user interface for configuring each unit operation in a sequence of unit operations will be described in more detail with respect to FIGS. 2A-2B.

For example, steps of a unit operation can include pre-run actions that prepare for the unit operation transformation. For example, a unit operation can define checks to be performed, equipment settings that need to be set, or any other appropriate actions to satisfy initial conditions of the unit operation, e.g., a material reaching a particular temperature.

Steps of a unit operation can also include one or more run actions that represent the actions of the core transformation. For example, run actions can include performing a chemical reaction, mixing materials, or any other appropriate transformation action.

Steps of a unit operation can also include one or more post-run actions that close down the unit operation after the transformation has been performed. For example, post-run actions can include actions for clean-up, data recordation, and results of post-transformation analysis, to name just a few examples.

The system 100 can receive the sequence of unit operation objects in a recipe from a user interface 120 by way of a user interface presentation 120 and can maintain each of the unit operations in the recipe using an electronic laboratory notebook subsystem 170. For example, the subsystem 170 can store a recipe object that includes each of the unit operations with corresponding parameters in a recipe database 130. For example, the parameters can include material input, material output, step, equipment, and bioprocess parameters pertaining to a particular unit operation. Each recipe object in the recipe database 130 can be associated with one or more electronic laboratory notebook objects generated for each step during recipe execution, as will be described in more detail below.

In addition, the system 100 can provide a recipe execution tool 114 for a user to execute a bioprocess, e.g., using the template provided by a recipe object stored in the recipe database 130 of the electronic lab notebook subsystem 170. For example, the system 100 can generate a worksheet representing laboratory effects of performing a particular step of a unit operation, e.g., a worksheet representing the workflow as parameterized by the parameters for the unit operation.

The system can also provide a corresponding worksheet interface 125 to an end-user device, e.g., the end-user device 190, 195. The worksheet interface 125 can provide the necessary structure to support the configured bioprocess, e.g., the worksheet including the steps of the particular unit operation being executed, instructions, and material input, material output, result input, e.g., a result table, for capturing measurements or scientific results from the unit operation, etc., while supporting the modification of any component based on the actual execution of the step. As an example, a user can update the worksheet by way of the worksheet interface 125 with modifications to the plan encoded by the recipe object and result data during execution.

For example, the subsystem 170 can initialize a respective electronic laboratory notebook object for each step of each unit operation in the recipe database 130 for a particular execution of the recipe. The system 100 can then maintain the electronic laboratory notebook objects in the electronic laboratory notebook database 175 and update the corresponding electronic laboratory notebook objects using notes, modifications, and results entered by a user by way of the worksheet interface 125 during the recipe execution.

In particular, the system 100 can generate an electronic laboratory notebook object for a particular step of a given execution of the recipe, can store the electronic laboratory notebook object in the electronic laboratory notebook database 175, and can provide a corresponding worksheet interface 125 for the electronic laboratory notebook object to a user. The system 100 can then receive data related to the execution of the step by way of the worksheet interface 125 and can update the underlying electronic laboratory notebook object in the database 175 to memorialize the particular execution of the recipe.

In some cases, the system 100 can receive notes, modifications, and results from multiple users using the worksheet interface 125. For example, the system 100 can receive execution data from the user of end-user device A 190 and the user of end-user device B 195 by way of the worksheet interface 125.

As an example, the worksheet interface 125 can include a notebook panel with one or more display portions, e.g., display portions including instructions for the step, one or more tables providing material inputs, material outputs, bioprocess parameters, or necessary equipment for performing the step represented by the worksheet, and a results table for the capturing of results data. The worksheet interface 125 can allow for rich-formatted text, photos of lab setup, attachments like excel spreadsheets, etc. to be integrated directly in the worksheet, e.g., as opposed to being attached to a form that represents the step. An example of a worksheet user interface will be described in more detail with respect to FIGS. 4A-4C.

The worksheet interface 125 can be auto-populated, e.g., the system 100 can provide data relating to certain aspects of the worksheet interface 125 in the worksheet interface 125 using data stored in one or more of the electronic laboratory notebook object database 175, e.g., from data entered with respect to prior executed steps using the recipe execution tool 114, a lab equipment, inventory, and sample database 140 that stores up-to-date information about a state of the equipment in a given laboratory, or a results database 150. In particular, the system 100 can populate one or more fields in a worksheet corresponding to the obtained data.

As another example, the system 100 can populate the worksheet interface 125 with the default setpoint values for one or more of material inputs, equipment, or bioprocess parameters as specified by the recipe configuration. As yet another example, the system 100 can populate the worksheet interface 125 with variant setpoint values that override the default values specified by the recipe. An example for configuring variant values will be described in more detail with respect to FIG. 3B.

For example, the system 100 can receive an indication that a next step of the unit operation has been initiated, e.g., from a user submitting results in the worksheet by the way of the worksheet interface 125 of a previous step. In this case, the system 100 can automatically populate execution data from the previous step into a second worksheet corresponding to the next step of the first operation. As another example, in response to receiving an indication that a final step of the unit operation has concluded, the system can automatically initiate the first step of the next unit operation.

In some cases, autopopulating data in the worksheet interface 125 can involve the system 100 obtaining data from the lab equipment, inventory, and sample database 140 that includes the currently available samples 145(*a*), vials and other glassware 145(*b*), and assay plates 145(*c*), and other expendable equipment 145(*n*) at hand in a laboratory that the users are in. As an example, the system 100 can autopopulate information about the one or more input materials required to perform the step.

In another case, autopopulating data in the worksheet interface 125 can involve the system 100 obtaining data from a results database 150 that stores data readings from one or more laboratory equipment systems, e.g., a polymerase chain reaction machine, centrifuge, spectrophotometer, flow cytometer, gel electrophoresis device, etc. For example, the system 100 can provide one or more endpoints for the electronic components of the device and can be configured to receive data from the laboratory equipment systems involved in each step of the unit operation. In this case, the system 100 can obtain output data for the previous step of the unit operation and can populate the next worksheet with the output data. In some cases, the execution data can include container transfer information representing substances transferred from one container to another, e.g., as a transition between the previous step and the next step.

In some cases, the laboratory equipment, inventory, and sample database 140 and results database 150 are included in a laboratory information management system (LIMS) 160, e.g., as depicted in the example system 100. In other cases, the laboratory equipment, inventory, and sample database 140, results database 150, and electronic laboratory notebook object subsystem 170 are included in a laboratory information management system (LIMS) 160.

For example, the LIMS 160 can be configured to manage data pertaining to samples, e.g., including sample collection data, disposal data, labelling, and storage information, result data, analysis data, inventory management data, equipment data, etc. As another example, the LIMS 160 can be configured to create an audit trail, e.g., a record documenting data creation, modification, or deletion, with respect to capturing regulatory compliance and security data.

More specifically, the system 100 can generate an electronic laboratory notebook object for each step of each unit operation using a particular step of a recipe object each time that the recipe execution tool 114 is used to execute the step. An example of configuring recipe execution using the recipe execution tool 114 will be described in more detail with respect to FIGS. 3A and 3B. The generated electronic laboratory notebook objects can provide a persistent record of operations in a laboratory for each experimental run. In some cases, the experimental runs can be further memorialized using the LIMS 160, e.g., by associating the electronic laboratory notebook objects with corresponding data from the laboratory equipment, inventory, and sample database 140 and the results database 150.

The system 100 can employ the recipe execution tool 114 to generate worksheets, respective electronic laboratory notebook objects, and can provide corresponding worksheet interfaces 125 for each of the unit operations in the recipe to support execution of a batch, e.g., all unit operations of a recipe. As an example, one or more batches can be performed as part of a study that involves the modification of one or more steps of the recipe to create different variants.

The system 100 can also store all data generated during execution of the batch as a batch record, e.g., by associating the electronic laboratory notebook objects in the batch with a batch identifier in the electronic laboratory notebook object database 175. As an example, the batch identifier can be the identifier for the vial or container of the sample used in the batch. As another example, the batch identifier can be a randomly generated identifier. In this case, each batch record includes instances of a unit operation, e.g., based on the particular electronic laboratory notebook object stored for the unit operation of the batch, that include data generated from a particular execution of the recipe.

Furthermore, in operation, a user can use the recipe execution tool 150 to design different variations of a bioprocess using the bioprocess template provided by the recipe, e.g., by varying the bioprocess parameters. In this specification, a recipe variant is a recipe that captures modifications in parameters from an original recipe. For example, the recipe execution tool 150 can automatically or with some process-design user input generate multiple different recipe variants with different variations of their bioprocess parameters. An example of designing a study including two variants of a bioprocess will be described in more detail with respect to FIG. 3B.

For example, the system 100 can allow for the organization of multiple iterations of a single step within an experiment, e.g., since the system 100 can generate an electronic laboratory notebook object for each iteration in the electronic laboratory notebook object database 175. As another example, the system 100 can allow for the varying of default values of bioprocess parameters encoded in the worksheet to generate multiple copies of the worksheet for different experimental conditions.

As yet another example, the system 100 can allow for the organization of results produced at different times or as part of different rounds of performing the same experiment, e.g., since the system 100 can generate corresponding electronic laboratory notebook objects for each round of the same experiment. In some cases, the electronic laboratory notebook objects can additionally include metadata pertaining to a date, month, time of execution, and an experiment identifier, e.g., that can be used to unify the electronic laboratory notebook objects pertaining to a particular batch execution of the bioprocess in the electronic laboratory notebook object database 175.

Additionally, the system 100 can provide a bioprocess review tool 116, e.g., for a user that did not perform the step of the unit operation to review the contents of the experiment that pertain to the particular step. For example, the user of the end-user device A 190 can perform one or more steps of the unit operation, e.g., using the worksheet interface 125 provided by the recipe execution tool 114, and the user of the end-user device B 190 can review one or more steps of the performed unit operation(s) using the bioprocess review tool 116.

In this case, a user can submit a request for bioprocess review and the system 100 can prevent any further modification of the electronic laboratory notebook objects corresponding with the request for bioprocess review until another user has performed the review. For example, the system 100 can identify and access the corresponding electronic laboratory notebook objects for a particular request in the electronic laboratory notebook object database 175 and provide them to the user that made the request for bioprocess review.

By maintaining the electronic laboratory notebook objects in an electronic laboratory notebook object database 175, the system 100 can provide a persistent record of experiments that are run using the recipe execution tool 114 for experiment repeatability and compliance. In particular, the system 100 is configured such that any modifications made at execution time can be memorialized in an electronic laboratory notebook object that captures a record of what happened as the experiment was being executed. The system 100 can retain the electronic laboratory notebook objects generated for each unit operation as specific instances of the unit operation, while preserving the underlying recipe object in the recipe database 130, e.g., for worksheet and corresponding electronic laboratory notebook object initialization.

The system 100 can also identify and access a particular laboratory notebook object in the database 175 using the electronic laboratory notebook subsystem 170 in response to a user request to access the particular laboratory notebook object, e.g., without employing the bioprocess review tool 116. The system 100 can then provide the particular laboratory notebook object for display on the user device. In some cases, the system 100 can provide a dashboard visualization of multiple electronic laboratory notebook objects, e.g., in response to a user request to access all or a subset of two or more electronic laboratory notebook objects for a particular step of a unit operation.

Furthermore, the generated electronic laboratory notebook objects can be data structures that are compatible with other electronic laboratory notebook systems, e.g., the electronic laboratory notebook objects can have a standardized format or schema that can be accessed and viewed by other systems, e.g., the system 180 which is separate from the lab execution system 100. The ability of the electronic laboratory notebook objects to be used by other systems facilitates the transfer of experimental data relating to bioprocess execution and results to another location.

For example, the system 180 can be the system of a different laboratory or production facility. The system 180 can receive or access and view the electronic laboratory notebook objects without having access to the electronic laboratory notebook subsystem 170, e.g., the electronic laboratory notebook subsystem 170 can transmit one or more of the electronic laboratory notebook objects to the other electronic laboratory notebook system 180.

In some cases, the other electronic laboratory notebook system 180 can provide the received electronic laboratory notebook objects for display on a user device. For example, the other system 180 can employ corresponding worksheet interfaces or other user interfaces to a user device that does not have access to the underlying electronic laboratory notebook subsystem 170 to provide a worksheet to a user, e.g., by way of an application programming interface (API). The system 180 can receive data for updating the electronic laboratory notebook objects by way of the worksheet interfaces or the other user interfaces.

The reusability of the electronic laboratory notebook objects can assist in the technology transfer necessary from a research facility to a production facility for a candidate production process. Moreover, the persistence of the electronic laboratory notebook objects can enhance accountability by providing the documentation necessary for repeating an experiment, e.g., in a different laboratory.

More specifically, the electronic lab notebook subsystem 170 can provide batch results to another electronic lab notebook system 180, which can represent what parameters were actually used and what actually happened during execution of the batch as well as the properties of any resulting or intermediate materials used or produced. The batch results can record what operators did as they did it, as well as results of analytical tests, e.g., assays, performed on samples taken of the material as it is produced.

Data about executed batches can be converted to and exported in analysis-ready datasets to support the scientific analysis required to assess and compare the relative performance of batches, and their corresponding recipe variants, on dimensions such as productivity or quality. The standardized recipe data model makes these comparisons easier and more intuitive. Such comparisons can include comparing multiple batches within an experiment, or batches performed at different times in different experiments.

For example, the system can access result data that pertains to a number of executions, e.g., from multiple batches in a study, and can provide a data analysis user interface, e.g., a dashboard user interface, to visualize the data, e.g., as a table or using one or more graphs. As an example, the user interface can support the filtering, sorting, or application of analytic algorithms to the data and can provide one or more tools for graphing the data, e.g., a line graph, box-and-whisker plot tool, etc., to visualize results of different executions. In particular, the system 100 can provide a configurable visualization of multiple executions to allow for the analysis of outcome, efficiency, and efficacy trends regarding each variant of the recipe.

Figure 2A:
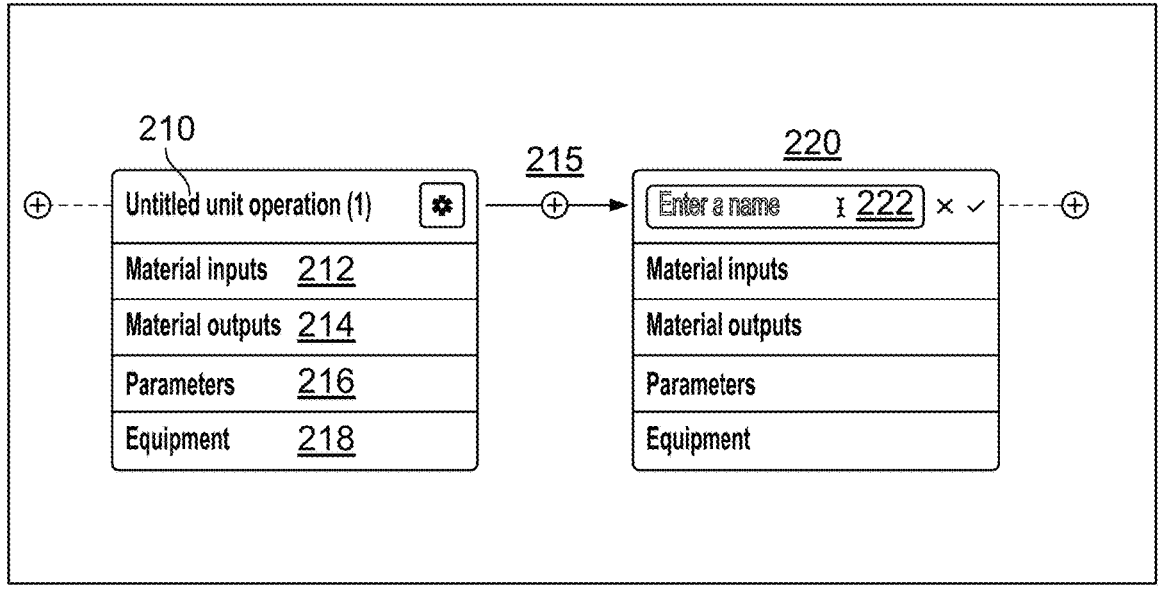
FIGS. 2A and 2B illustrate example user interface displays for designing a recipe.
Figure 2B:
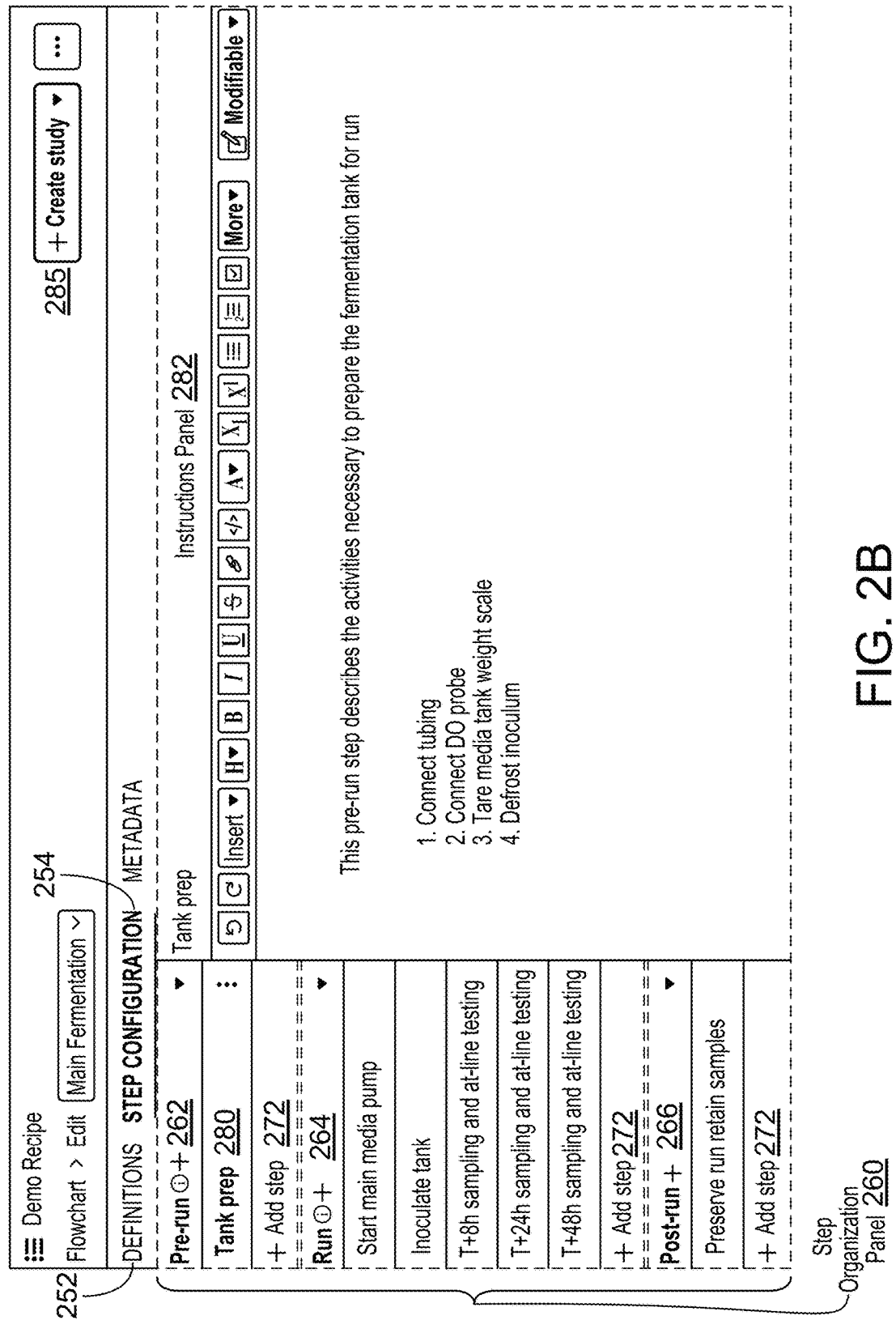

FIGS. 2A and 2B illustrate example user interface displays in a user flow for designing a recipe. As an example, the lab execution platform system 100 can provide the user interface displays 200, 230, and 250 to an end-user device as part of the recipe design tool 112.

FIG. 2A illustrates a user interface display for generating the recipe. In particular, the system can provide the recipe configuration displays 200 and 230 for a user to configure the sequence of unit operations in a recipe.

For example, the system can provide the recipe configuration display 200 for a user to configure a recipe using one or more unit operation objects. Each unit operation defines one or more steps to be performed. Each step represents an action to be performed as well as whether and what type of data to be recorded after the step is completed.

In the particular example depicted, the display 200 can allow for a user to create, label, e.g., by entering a name into a text input portion 222, and arrange a set of unit operation objects, e.g., the objects 210 and 220, using one or more links, e.g., the link 215, for connecting the unit operation objects, e.g., into the sequence of unit operation objects in a recipe. While depicted in a linear arrangement in this example, the links can allow for the arrangement of the unit operation objects in any configuration, e.g., a graph, that establishes a sequence, e.g., including repeated unit operations.

In general, unit operations have the following primary categories of data: bioprocess parameters, material inputs, equipment requirements, material outputs, and steps. Therefore, each of the unit operation objects includes a respective input portion for material inputs 212, material outputs 214, bioprocess parameters 216, and equipment 218.

For example, upon receiving indication of a selection of a unit operation object, e.g., the unit operation object 210 or 220, the system can provide the recipe configuration display 230 to a user to receive the relevant material input 232, material output 234, bioprocess parameters 236, and equipment 238 data. In the particular example depicted, the recipe configuration display 230 can provide the respective tables 232, 234, 236, and 238 to facilitate data entry.

Each material input 232 can have one or more fields to represent the materials that are used for the unit operation. Material inputs 232 can for example have fields including a name, a type, a parent entity from which the material was derived, a child entity, a quantity, a unit, and a description, to name just a few examples.

Each material output 234 can have one or more fields to represent a material produced by executing the unit operation. Material outputs 234 can for example have fields including a name, a material output schema, e.g., regarding quantity, which containers hold the material, or any other appropriate property of the output material, and a description.

Each parameter 236 can have one or more fields specifying (i) an operating point parameter to represent the conditions to be used for execution of the unit operation or (ii) a control parameter specifying the configuration of the equipment, e.g., stirring revolutions per minute. Parameters 236 can for example have fields including a parameter name, a type, a setpoint, a unit, a minimum, a maximum, and a description, to name just a few examples.

As an example, temperature and pH settings are operating point parameters that govern the bioprocess as a whole. In some cases, the operating point parameters can be maintained by periodic manual intervention, e.g., by adding ingredients, diluting the mixture, etc. In other cases, the operating point parameters can be maintained automatically by a multi-equipment system operating in a feedback loop, e.g., the combination of a thermostat probe inserted into a tank, computer or programmable logic controller, and a device to heat or cool the tank in accordance with the measured temperature provided by the probe.

Each equipment requirement 238 can have fields to represent features or capabilities of equipment needed to execute the unit operation. Equipment requirements 238 can have one or more fields including a name, a capability, a size, and a description, to name just a few. For example, equipment requirements 238 can include the make and model of an exact equipment type, e.g., "Eppendorf Research Plus Adjustable Volume, Single Channel Pipette, 20-200 µL".

In order to provide greater flexibility, the system can allow for the equipment requirements of a unit operation to be equipment-agnostic. In other words, the equipment requirements 238 can specify the required capabilities or properties of equipment needed to perform the unit operation, but without specifying a particular device or machine or a particular model or name of a machine. As another example, equipment requirements 238 can include other parameters that can be used to select a valid piece of equipment given multiple available potentially-equivalent equipment types, e.g., a pipette with a particular aspiration volume range of 20-200 µL, and a specified max systematic transfer error of ±0.6%. In this way, the recipe can remain untethered to the particular environment of a specific location, e.g., a process development facility.

FIG. 2B illustrates a user interface display for configuring one or more steps of each unit operation. For example, the step configuration display 250 can be provided to a user for the specification of each step in a unit operation. In the particular example depicted, the recipe configuration displays 200, 230 of FIG. 2A can be displayed in response to the selection of the definitions tab 252 and the step configuration display 250 can be displayed in response to the selection of the step configuration tab 254.

Each step can have fields to represent an action to be performed to execute part of the unit operation. Each step represents the performance of an action by an actor in the laboratory. Thus, each step can be configured to record to whom the action is assigned, a time stamp of when the action was performed or initiated, as well as a status of the action. For example, an action can be incomplete, complete, failed, or successful, to name just a few examples.

As an example, the step configuration display 250 can include a step organization panel 260 that displays the one or more configured steps of a unit operation. In this case, the one or more configured steps are organized into different major phases of the unit operation as step groups, e.g., a pre-run 262, run 264, and post-run 266 step group. In this case, the step groups form a hierarchical outline of the actions to perform. While there is only two levels of hierarchy in the example depicted, the system can be configured to support additional levels of hierarchy.

Each step group includes one or more steps, e.g., the pre-run step group 262 includes the tank prep step 280, the run step group 264 includes the start main media pump, inoculate tank, and sampling steps at different time durations, and the post-run step group 266 includes the retention of samples step. The system can allow a user to add steps to the unit operation, e.g. using an add step button 272. In this particular example, the system can allow a user to add a step to the pre-run 262, run 264, and post-run 266 step groups.

In some implementations, each step can specify at least part of the worksheet that will be initialized and provided to a user by way of a corresponding worksheet interface to memorialize the execution of the step during an experiment. In the particular example depicted, a user is configuring the tank prep step 280 using an instructions panel 282. In this case, the user is inputting text into a text input portion of the instructions panel 282 that will be rendered directly as part of the worksheet interface for the step 280.

For example, the instructions panel 282 can be configured to include operation instructions and data recording aids specific to that step. In this case, the instructions panel 282 includes only text instructions. In some cases, the instructions panel 282 can be configured to include rich-text formatting. As another example, the instructions panel for a result recording step can include a results table. As yet another example, the instructions panel for an assay preparation step can include an assay visualization. The system can allow the text or other data included in the instructions panel 282 to be modified in place.

After the system receives the sequence of unit operations in the recipe and their corresponding data, e.g., the material inputs, material outputs, bioprocess parameters, equipment, and steps as specified using the step configuration display 250, the system can store each of the unit operations in the sequence of unit operations in the electronic laboratory notebook subsystem, e.g., in a recipe object stored in the recipe database 130. As described with respect to FIG. 1, each electronic laboratory notebook object can be initialized from a step of a particular stored unit operation and can be associated with the particular stored unit operation in the electronic laboratory notebook subsystem.

Furthermore, in some implementations, the system can support the creation of a study, e.g., the configuration of the execution of one or more batches of the recipe. In some cases, one or more of the batches can include configured variants of the recipe, e.g., where at least one step of a unit operation has been modified as part of an experiment to analyze the impact of the change on the bioprocess output, efficacy of the change, or both. For example, the system can provide a user flow for configuring a study based on an underlying recipe object as part of the recipe execution tool 114, e.g., in response to the selection of the create study button 285.

Figure 3A:
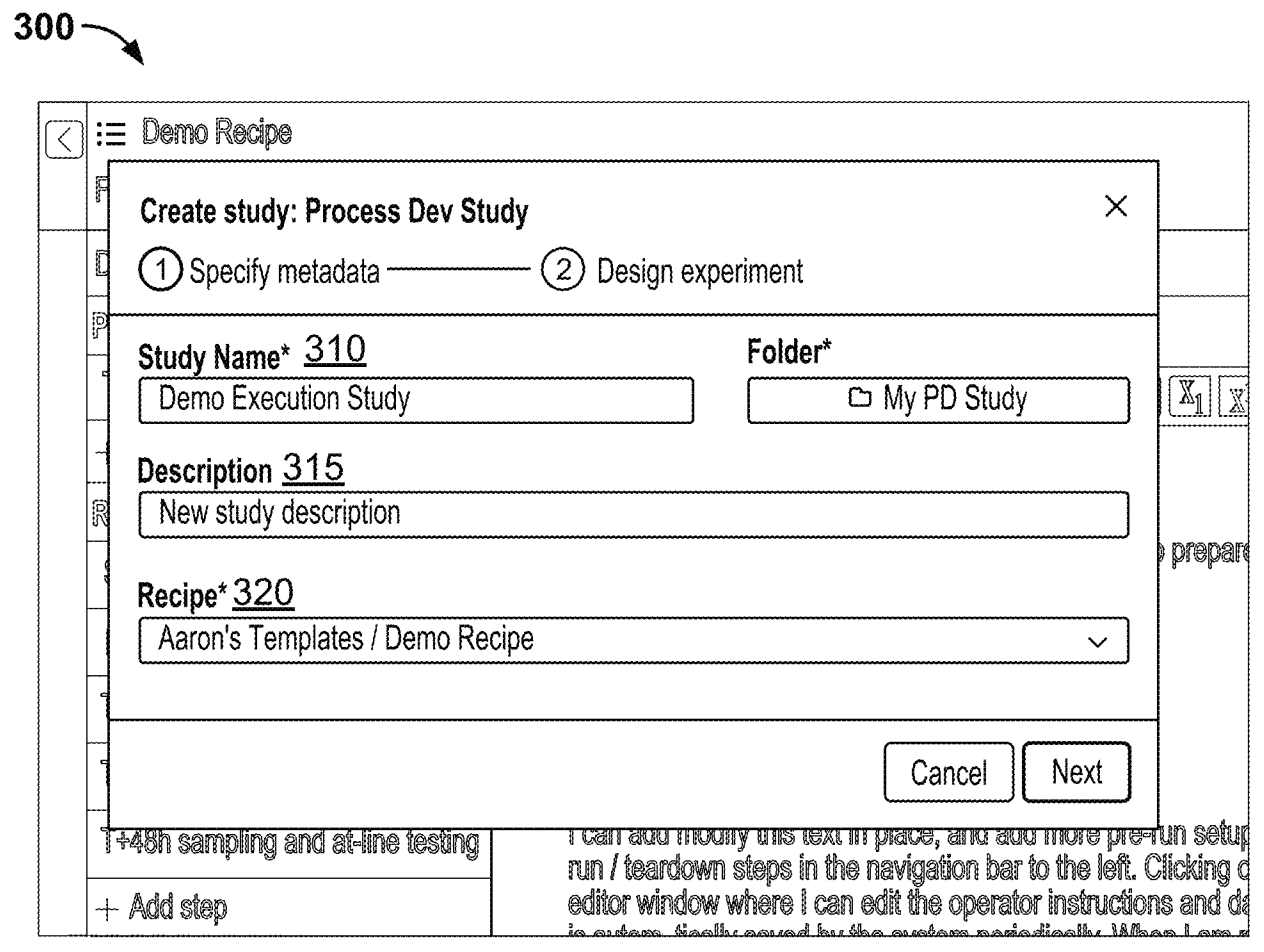

FIG. 3A illustrates a first user interface display in the user flow for creating a study. The user interface display 300 includes respective text input portions for specifying the name of the study 310, a description 315 of the study, and a menu for locating the recipe 320, e.g., the underlying recipe object, that will be used for the study. For example, the user interface 300 can provide an option for a user to select a recipe, e.g., an already existing recipe from the recipe database 130 of the system, using a drop-down menu. In the case that a user selects an already existing recipe, the system can access the underlying recipe object and provide the recipe to the user, e.g., for variant modifications, as will be described below.

The system can then provide the study configuration display 350 as depicted in FIG. 3B for the configuration of a study based on the underlying recipe object for the selected recipe 320. As an example, a user can use the study configuration display 350 to configure a study including a number of parallel or sequential whole batch executions of all the unit operations, e.g., an experiment A and B performed sequentially as A before B or in parallel, with the material inputs, material outputs, bioprocess parameters, equipment, and steps from the underlying recipe object of the selected recipe 320.

As another example, a user can use the study configuration display 350 to configure one or more parallel or sequential batch executions of variants of the underlying recipe object. In this case, the bioprocess parameters can be specified by a process designer and indicate how recipe variants should be generated from the selected recipe 320. For example, the bioprocess parameters can indicate four different setpoints for a pH value used during a particular unit operation of the recipe. In this case, the system can generate different recipe variants that reflect the different pH setpoints in execution.

In the particular example depicted, the study is configured to include two variants, a low temperature variant 362 and a high temperature variant 364, for a main fermentation 370 unit operation, e.g., which have been specified in a variant specification 360 portion of the study configuration display 350. In this case, the batch execution will feature two batches: a low temperature batch featuring the low temperature variant 362 of the main fermentation step 370 and a high temperature batch featuring the high temperature variant 364 of the main fermentation step 370.

For example, a user can configure which of the material inputs, material outputs, bioprocess parameters, equipment, and steps from the underlying recipe object of the selected recipe 320 should be overridden by variant parameters. In particular, the display 350 allows for the indication of default values 375, e.g., values that will remain unchanged during recipe execution of the two variants 362 and 364, and variant values 380, e.g., values that deviate from the default parameters 375 specified by the underlying recipe object.

In this particular example, the tank temperature is configured to deviate from the default value 375 at which the main fermentation 370 unit operation is supposed to occur according to the temperature value stored in the underlying recipe object. For example, the low temperature variant 362 is specified to be executed at a tank temperature of 36 C and the high temperature variant 364 is specified to be executed at a tank temperature of 40 C.

After configuring the study, the user can select the execute button 390 to indicate that the user is ready to execute the study. After receiving this indication, the system can automatically generate the worksheets necessary to execute the study, e.g., according to the default and variant values of the parameters. More specifically, since the study configuration display 350 allows for the varying of default values encoded in the underlying recipe object, the system can generate multiple copies of the worksheet for different experimental conditions, e.g., as represented by each variant 362 and 364.

Figure 4A:
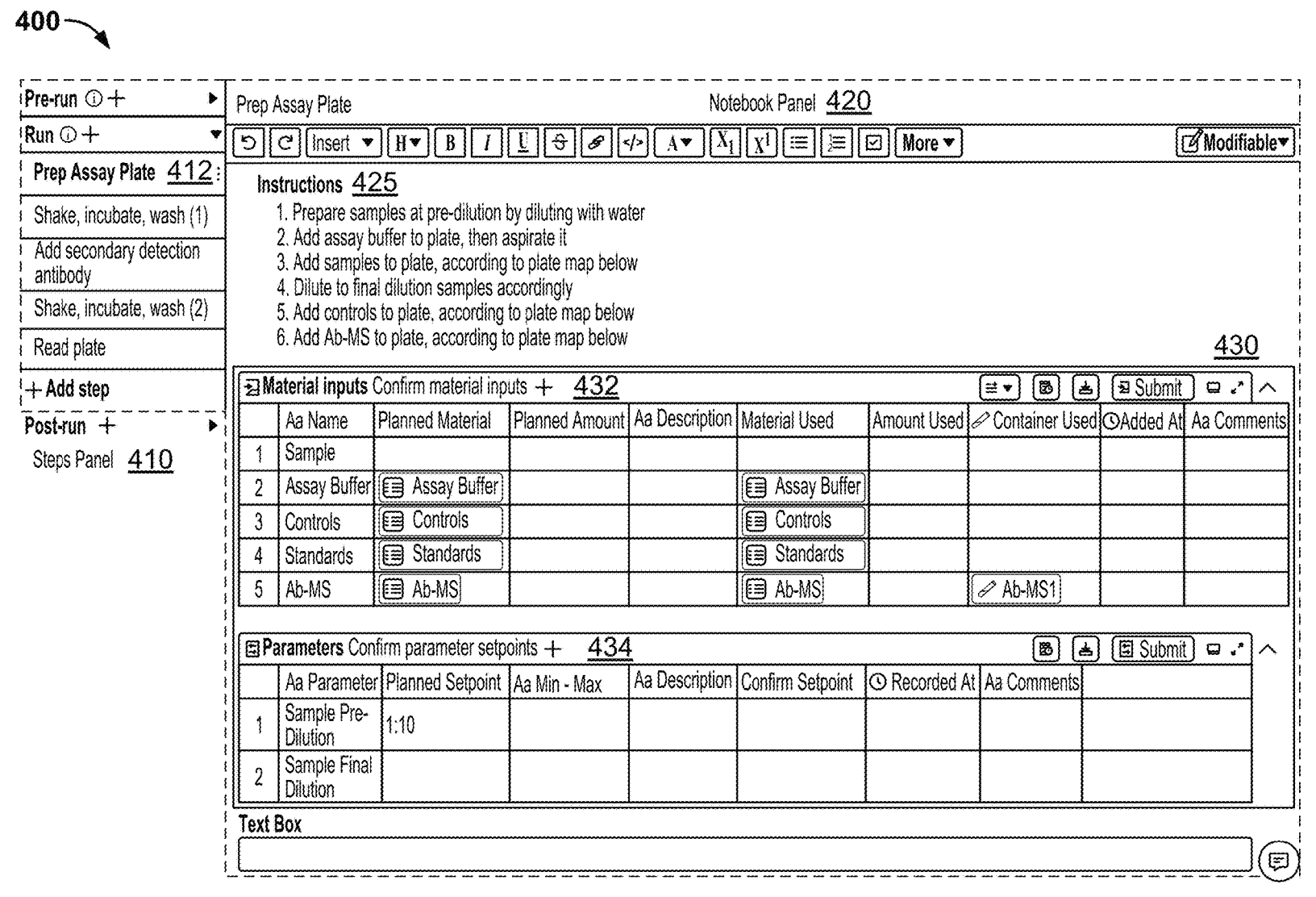
Figure 4B:
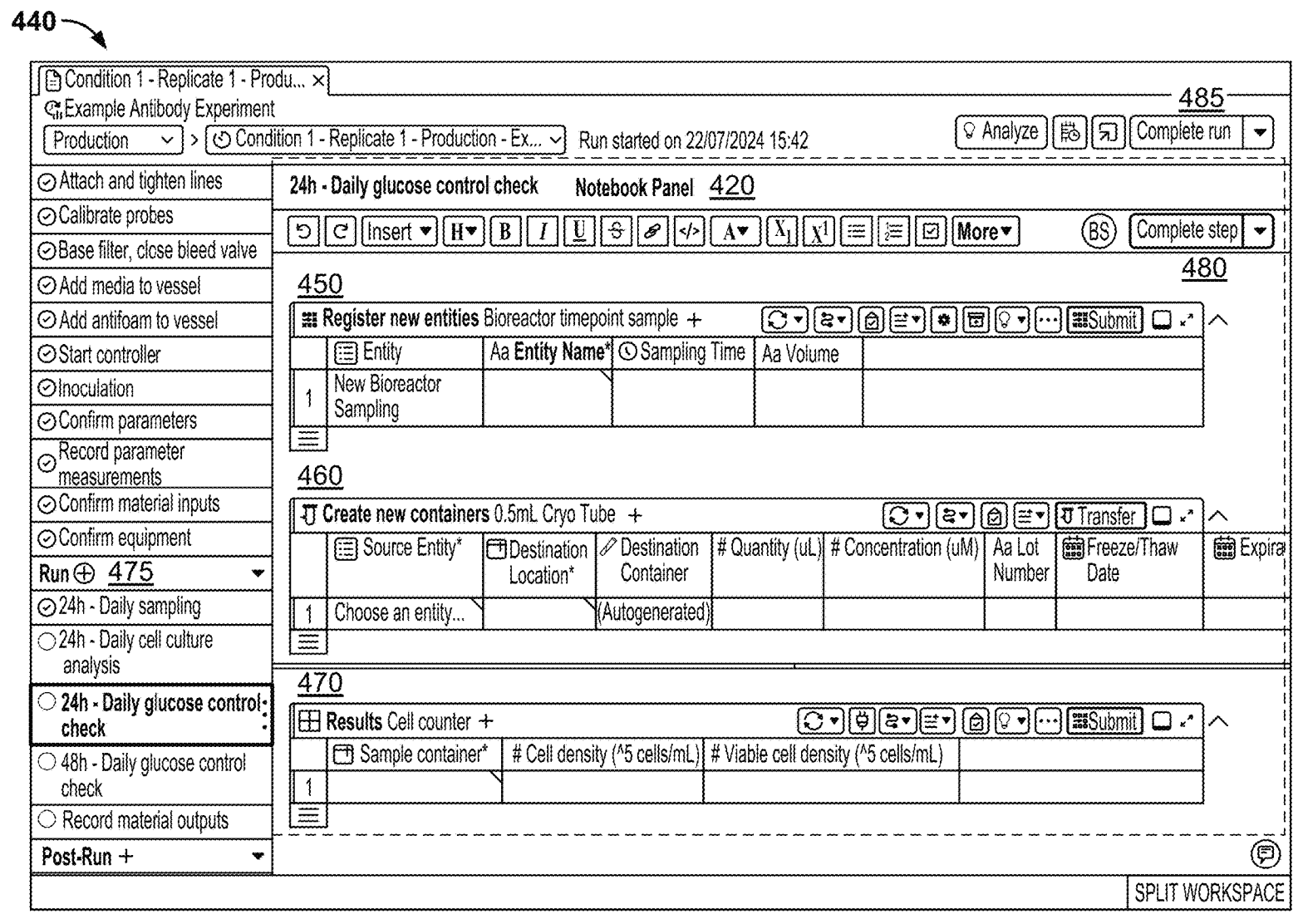
Figure 4C:
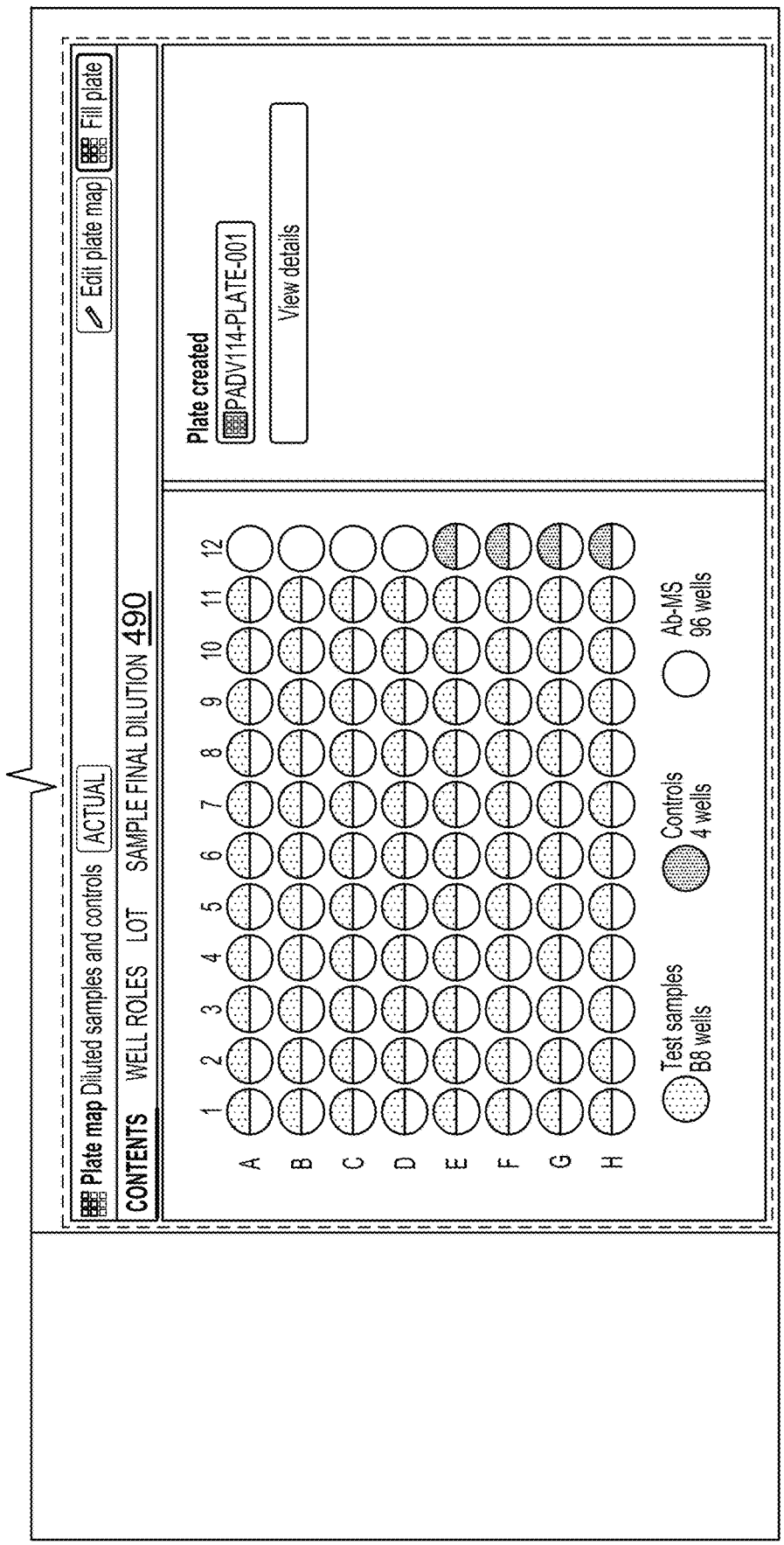

FIGS. 4A, 4B, and 4C illustrate example user interface displays for corresponding worksheet interfaces initialized from a step of a recipe. As an example, the lab execution platform system 100 can provide the user interface displays 400, 440, and 480 to an end-user device as part of the recipe execution tool 114, e.g., as part of a study.

FIG. 4A depicts an example worksheet interface 400. In the particular example depicted, the worksheet interface 400 includes a steps panel 410, where each tab represents a step in the unit operation. The system can generate each worksheet and allow a user to navigate to a particular step using the steps panel 410. As an example, the steps panel 410 can include a selector for navigating to a particular step. In this case, the highlighted tab, e.g., the selected tab 412 corresponds with the content displayed in the notebook panel 420, which is juxtaposed with the steps panel 410.

For example, at each step of each unit operation, the recipe execution tool can generate or provide a user interface presentation for the step. In particular, the system can generate a worksheet interface that provides a worksheet including the parameters, material inputs, equipment requirements, material outputs, and instructions for the step. After each step of the unit operation is performed, the recipe execution tool can record data used for the step, e.g., a temperature setting, as well as data generated by the step, e.g., the temperature actually used. The data can be recorded by way of the worksheet interface 400 (and 440, 480).

For example, the notebook panel 420 can be configured to include a text display portion 425 and a table display portion 430. In the particular example depicted, the text display portion 425 includes instruction data that can inform the completion of the step. The text display portion 425 can also be configured for the upload and integration of rich-formatted text, photos of lab setup, and the display of relevant objects from the system, e.g., the display of an assay object, as will be described with respect to FIG. 4C.

In the particular example depicted, the table display portion 430 includes a material input table 432 and a parameter 434 table. As an example, the system can access the instruction data, material input data, and parameter data that is stored as part of the unit operation in the recipe database 130 and can display the data in respective tables, e.g., when the worksheet is initialized by the electronic laboratory notebook subsystem. As another example, the system can allow for the upload and linking of, e.g., with a read-only preview and option to download, or direct integration of excel spreadsheets or other related files for revision in the table display portion 430.

The actual conditions that occurred during execution of a recipe can often differ from the data pertaining to performing the step as encoded by the bioprocess parameters of the initially designed recipe. The system can allow for a user to modify or add an additional step to the unit operation at run-time, e.g., by way of the worksheet interface 400 (and 440, 480). Since the user updating the worksheet interface results in the system modifying or generating a corresponding electronic laboratory notebook object, the system can memorialize the update to the step for the particular execution of the step in a corresponding electronic laboratory notebook object.

For example, the data in the tables 432 and 434 can be editable, e.g., such that a user can keep track of any revisions to the plan encoded by the recipe during execution. As an example, the user can elect to use different laboratory equipment or a different control material in the event that one or more pieces of equipment specified in the step are not available.

The notebook panel 420 can also be configured to include a results display portion, e.g., as displayed in example worksheet interface 440 in FIG. 4B. In particular, the worksheet interface 440 includes a results table 470 for capturing results data, a registration table 450 for logging new biological samples into the lab information management system 160, and a container table 460 for specifying the location of the new entities. In some cases, data from the registration table 450 and the container table 460 can be added to the lab equipment inventory database 140, e.g., as samples 145(a) data. For example, a user can register samples or genetic sequences in the system and another user can access information about the samples or genetic sequences including their location, the make, model, manufacturer of the storage container, volume and concentration of the sample aliquot in the container, e.g., as part of another bioprocess.

As an example, the system can automatically record results from one or more laboratory equipment systems involved in each step of a unit operation. In some cases, the system can be configured to receive and update the actual result values, e.g., over time, on the worksheet interface. For example, the system can generate actual result values at every 1 second, 5 seconds, or 100 seconds, to name just a few examples. As an example, a thermometer or a probe can generate the actual temperature used for a step of a particular unit operation, and the system can record those values that actually occurred during the batch.

In some cases, the system can allow a user to add steps to the unit operation during execution time, e.g., using the add step button 475. As another example, the system can configure a study based on a recipe that was modified at execution time, e.g., by a user adding one or more steps to the corresponding unit operation using the add step button 475 in the step configuration display. In the case that a user adds one or more additional steps, the system can initialize corresponding electronic laboratory notebook objects for the additional steps and update the recipe object, e.g., in the electronic laboratory notebook subsystem 170, to reflect the modification at execution time. As an example, the system can update the corresponding electronic laboratory notebook object in response to the addition of a step with the button 475, or can periodically update the corresponding electronic laboratory notebook object as a user makes execution modifications.

After the corresponding electronic laboratory notebook object has been updated, the system can support the execution of a batch of experiments based on the updated method. Furthermore, in some cases, the system can support the generation of further experiments based on modifying the updated method, e.g., to provide an experimental version control.

In the particular example depicted, the system can allow the user to indicate the completion of a step 480 or of the unit operation 485. After receiving the indication of the completion of the step 480, the system can modify the underlying electronic laboratory notebook object corresponding with the worksheet for the step. After receiving the indication of the completion of the unit operation 485, the system can advance to the corresponding worksheet interface for the next step. At the completion of the final unit operation, the system can be configured, e.g., by a user, to initiate another run or provide result data that pertain to a number of runs, e.g., in a dashboard as described with respect to FIG. 1.

In some cases, the notebook panel 420 can also be configured to include an assay display portion 490 that includes a representation of contents of one or more wells of a plate used in an assay, e.g., as displayed in example worksheet interface 480 in FIG. 4C. In this case, the system can allow for the registration of a plate template, e.g., as part of a step in a unit operation. For example, the plate template can include the number of wells, the planned buffer, and a specification of the wells that will be filled with samples.

The system can then autopopulate the plate schema in the assay display portion 490 to provide information about the planned materials for filling each well of the plate, and allow the user to record which samples they actually place into each well of the plate as part of executing the assay preparation step in the experiment.

Figure 5:
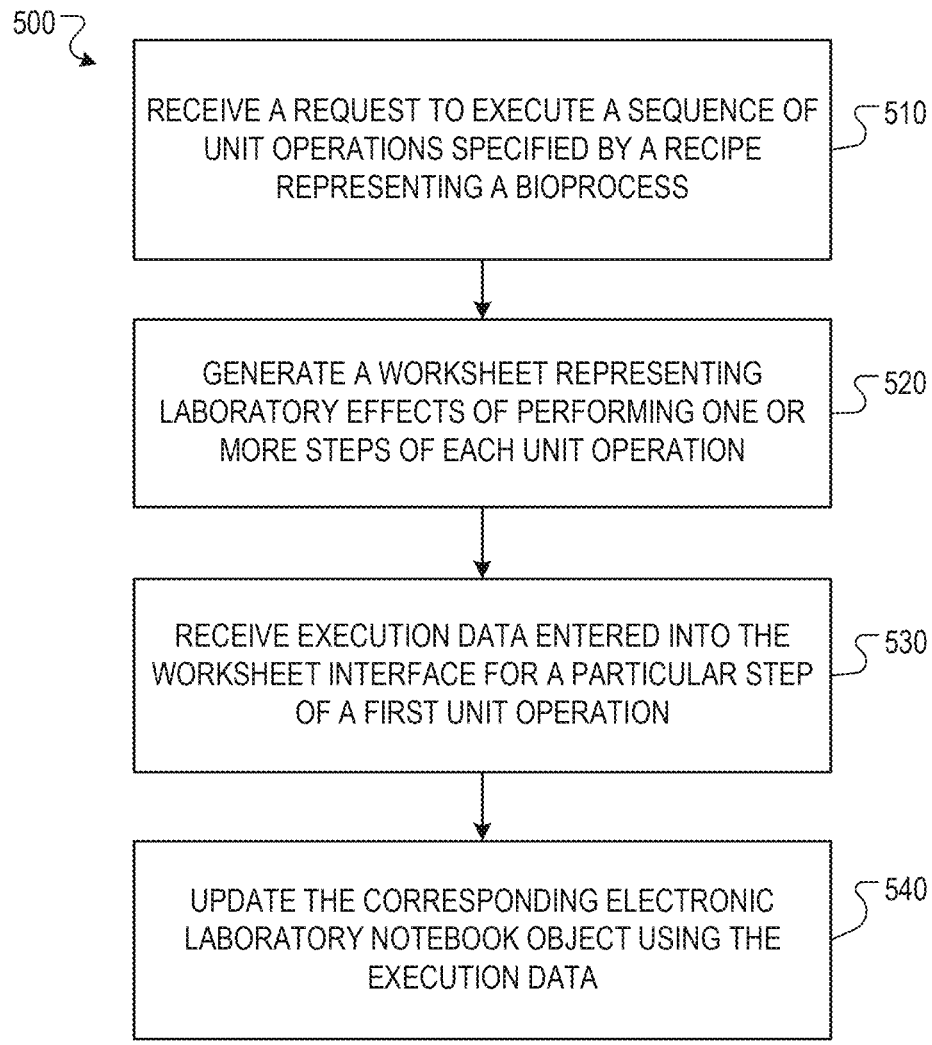
FIG. 5 is a flow diagram of an example process for executing a bioprocess from a recipe using the example lab execution platform system.

FIG. 5 is a flow diagram of an example process for executing a bioprocess from a recipe using the example lab execution platform system. For convenience, the process 500 will be described as being performed by a system of one or more computers located in one or more locations. For example, a lab execution system, e.g., the lab execution system 100 of FIG. 1, appropriately programmed in accordance with this specification, can perform the process 500.

The system can receive a request to execute a sequence of unit operations specified by a recipe representing a bioprocess (step 510). In particular, each unit operation can define one or more steps to be performed. As an example, the system can receive the sequence of unit operations in the recipe through a user-interface that is configured to allow a user to arrange a set of unit operations into an order using one or more links. The system can also receive relevant material input, material output, steps, process parameters, and equipment data for the unit operation, e.g., by way of the user interface. As an example, the request to execute can initiate an experiment specified by the particular material input, material output, steps, bioprocess parameters, and equipment data that have been configured in the recipe.

In some cases, the request to execute the recipe can be part of a design study, e.g., that includes one or more variants of the recipe. For example, a variant of the recipe can include variant data that deviates from the values of at least one default parameter used in at least one step of the sequence of unit operations specified by the recipe.

The system can generate a worksheet representing laboratory effects of performing one or more steps of each unit operation (step 520), e.g., as parameterized by the particular study configuration of the recipe. For example, the system can generate the worksheet and a corresponding electronic laboratory notebook object in an underlying electronic laboratory notebook subsystem for each step in each unit operation, e.g., the system can generate an ordered collection of electronic laboratory notebook objects, and can provide a worksheet interface for displaying and receiving execution data for the electronic laboratory notebook associated with a particular step, e.g., to a user. As an example, the system can initialize the worksheet for a step of a particular unit operation stored in the electronic laboratory notebook system.

The worksheet interfaces can facilitate the performance of the unit operation. For example, in response to receiving an indication that a next step of the first unit operation has been initiated, the system can automatically populate execution data from the first unit operation in a second worksheet corresponding to the next step of the first unit operation, e.g., by obtaining output data for the particular step and populating the second worksheet with the output data as the input to the next step. In some cases, the recently completed step causes a sample aliquot to be produced, and the next step requires the sample aliquot as a material input. As another example, in response to receiving an indication that the final step of the first unit operation has been concluded, the system can automatically initiate a first step of a second unit operation.

In some cases, automatically populating execution data can involve the system obtaining data readings from one or more laboratory equipment systems or from a database that stores up-to-date information about a state of a laboratory, e.g., up-to-date information about the current inventory of input materials in the laboratory, and populating one or more fields in the second worksheet corresponding to the obtained data.

As an example, the worksheet interface can include a steps panel that includes a set of tabs representing each step in the unit operation. In this case, a highlighted tab can correspond with the tab selected from the unit operation. As another example, the worksheet interface can include a notebook panel for displaying one or more display portions including instructions for the step, e.g., rich-formatted instructions, one or more tables corresponding with the configuration of the step in the unit operation, and a portion for displaying and entering results. In some cases, the worksheet interface can additionally include an assay display portion that includes a representation, e.g., a visualization, of the one or more wells of an assay plate.

The system can receive execution data entered into the worksheet interface for a particular step of a first unit operation (step 530), and the system can then update the corresponding electronic laboratory notebook object using the execution data (step 540), e.g., using the electronic laboratory notebook subsystem. In some cases, a number of corresponding electronic laboratory notebook objects can be updated based on the execution data.

For example, a user can enter results data into the results display portion and the system can update the corresponding electronic laboratory notebook object to reflect the results. As another example, the user can modify the process represented by the worksheet interface in accordance with execution and the system can update the corresponding electronic laboratory notebook object to maintain a persistent record of the experiment as performed. As yet another example, the system can receive container transfer information representing a plate transfer or a non-plate transfer of a substance as part of the bioprocess.

In some cases, the system can access a particular laboratory notebook object, e.g., using the electronic laboratory notebook subsystem, in response to a request from an additional user and can provide the particular electronic laboratory notebook object for display by way of a worksheet interface on the user device of the additional user. As an example, the system can receive execution data from the additional user by way of the worksheet interface. As another example, the system can receive an indication of validation of the particular laboratory notebook object, e.g., as part of a peer review process undertaken by the additional user.

In some implementations, the generated electronic laboratory notebook objects can be compatible with one or more other electronic laboratory notebook systems, e.g., another system that does not have access to the underlying electronic laboratory notebook subsystem. In this case, the system can provide the electronic laboratory notebook object to the other system, e.g., for display by way of a worksheet interface or another interface. In particular, the system can allow for the facilitation of transfer of experimental data relating to bioprocess execution and results to another location using the electronic laboratory notebook objects. For example, the system can provide an application programming interface (API) that allows another location to access or download the electronic laboratory notebook objects.

While described here within the context of bioprocess control, the system of this specification can be applied within the context of other process control systems, e.g., in manufacturing, environmental control, water treatment, energy management and production, consumer product goods, food and beverage production, etc. The system can allow for the rapid iteration of different versions of a process, the maintenance of data relating to the process design phase, and the finalization of the process for production.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g., a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
  receiving a request to execute a sequence of unit operations specified by a recipe representing a bioprocess, wherein each unit operation defines one or more steps to be performed;
  generating, for each step of each unit operation, a worksheet representing laboratory effects of performing the step and having a worksheet interface for displaying bioprocess data and receiving execution data, including initializing, for each worksheet, a corresponding electronic laboratory notebook object in an underlying electronic laboratory notebook subsystem;
  receiving execution data entered into the worksheet interface for a particular step of a first unit operation; and
  updating, in the electronic laboratory notebook subsystem, the corresponding electronic laboratory notebook object using the execution data.

Embodiment 2 is the method of embodiment 1, wherein updating the corresponding electronic laboratory notebook object further comprises updating a plurality of corresponding electronic laboratory notebook objects in the electronic laboratory notebook subsystem using the execution data.

Embodiment 3 is the method of any one of claims 1-2, further comprising:
  receiving variant data that relates to at least one step of the sequence of unit operations specified by the recipe; and
  generating the worksheet representing laboratory effects of performing the at least one step in accordance with the variant data.

Embodiment 4 is the method of any one of claims 1-3, further comprising:
  receiving an indication that a next step of the first unit operation has been initiated;
  in response, automatically populating one or more of bioprocess data or execution data of a second worksheet corresponding to the next step of the first unit operation.

Embodiment 5 is the method of embodiment 4, further comprising:
  receiving an indication that a final step of the first unit operation has been concluded;
  in response, automatically initiating a first step of a second unit operation.

Embodiment 6 is the method of embodiment 4, wherein automatically populating execution data of the second worksheet comprises:
  obtaining data readings from one or more laboratory equipment systems; and
  populating fields in the second worksheet corresponding to the obtained data readings.

Embodiment 7 is the method of claim 4, wherein automatically populating bioprocess data comprises:
  obtaining data from a database that stores up-to-date information about a state of a laboratory; and
  populating fields in the second worksheet corresponding to the obtained data.

Embodiment 8 is the method of embodiment 7, wherein the data represents up-to-date inventory information about one or more input materials to the bioprocess.

Embodiment 9 is the method of embodiment 4, wherein automatically populating the execution data comprises:
  obtaining output data for the particular step of the first unit operation; and
  populating the second worksheet with the output data.

Embodiment 10 is the method of any one of embodiments 1-9, wherein the execution data comprises container transfer information representing substances transferred from one container to another.

Embodiment 11 is the method of any one of embodiments 1-10, wherein the electronic laboratory notebook object is compatible with one or more other electronic laboratory notebook systems.

Embodiment 12 is the method of embodiment 11, wherein the electronic laboratory notebook object is accessed using the one or more other electronic laboratory notebook systems.

Embodiment 13 is the method of embodiment 11, wherein the corresponding worksheet interface for displaying bioprocess data and receiving execution data is rendered on a user device that does not have access to the underlying electronic laboratory notebook subsystem.

Embodiment 14 is the method of any one of embodiments 1-13, further comprising:
  receiving, through a user-interface comprising a set of unit operation objects and one or more links for connecting unit operation objects, the sequence of unit operations specified by the recipe representing the bioprocess through an arrangement of the unit operations into an order using the one or more links;
  receiving corresponding data comprising one or more of material inputs, material outputs, bioprocess parameters, equipment, and steps for each unit operation object; and
  storing each of the unit operations in the sequence of unit operations specified by the recipe representing the bioprocess and the corresponding data in the electronic laboratory notebook subsystem, wherein each corresponding electronic laboratory notebook object is generated from a step of a particular stored unit operation and is associated with the particular stored unit operation in the electronic laboratory notebook subsystem.

Embodiment 15 is the method of any one of embodiments 1-14, wherein the worksheet interface for displaying bioprocess data and receiving execution data comprises:
  a steps panel comprising a set of tabs, wherein each tab represents a step in the unit operation, and wherein a particular tab is highlighted as a particular step selected from the unit operation;
  a notebook panel corresponding with the selected step, wherein the notebook panel is juxtaposed with the steps panel, and the notebook panel includes:
    a text display portion comprising instructions for the step,
    a table display portion comprising one or more of a material inputs table, a bioprocess parameter table, or an equipment table for displaying data pertaining to performing the step from the corresponding electronic laboratory notebook object and receiving execution data pertaining to the execution of the step by a user,
    an assay display portion comprising a representation of contents of one or more wells of an assay plate, or
    a results display portion for receiving and displaying results.

Embodiment 16 is the method of embodiment 15, wherein the text display portion further comprises rich-formatted instructions for the step.

Embodiment 17 is the method of any one of embodiments 1-14, further comprising:
  in response to a user request, accessing a particular laboratory notebook object using the electronic laboratory notebook subsystem; and
  providing the particular laboratory notebook object for display on a user device.

Embodiment 18 is the method of embodiment 17, further comprising receiving an indication of validation for the particular laboratory notebook object from the user device.

Embodiment 19 is the method of any one of embodiments 1-18, wherein receiving execution data entered into the worksheet interface for a particular step of a first unit operation comprises:
  receiving execution data from a first user device displaying the worksheet interface; and
  receiving execution data from a second user device displaying the worksheet interface.

Embodiment 20 is a system comprising: one or more computers and one or more storage devices storing instructions that are operable, when executed by the one or more computers, to cause the one or more computers to perform the method of any one of embodiments 1 to 19.

Embodiment 9 is a computer storage medium encoded with a computer program, the program comprising instructions that are operable, when executed by data processing apparatus, to cause the data processing apparatus to perform the method of any one of embodiments 1 to 19.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-implemented method comprising:
receiving, by a distributed laboratory execution platform system comprising a plurality of computers maintaining an electronic laboratory notebook database, a request to execute a sequence of unit operations specified by a recipe representing a bioprocess, wherein each unit operation defines one or more steps to be performed;
generating, for each step of each unit operation, a worksheet for each step of each unit operation representing laboratory effects of performing the step and having a worksheet interface for displaying bioprocess data and receiving execution data, including initializing, for each worksheet, a corresponding electronic laboratory notebook object in the electronic laboratory notebook database, wherein each corresponding electronic laboratory notebook object is generated from a step of a particular stored unit operation and is associated with the particular stored unit operation by the electronic laboratory notebook database;
receiving, by the plurality of computers in the distributed laboratory execution platform system, execution data entered into the worksheet interface for a particular step of a first unit operation;
updating, in the electronic laboratory notebook database, the corresponding electronic laboratory notebook object using the execution data; and
in response to receiving an indication that a next step of the first unit operation has been initiated, automatically populating one or more of bioprocess data or execution data of a second worksheet corresponding to the next step of the first unit operation using the electronic laboratory notebook database.

2. The method of claim 1, wherein updating the corresponding electronic laboratory notebook object further comprises updating a plurality of corresponding electronic laboratory notebook objects in the electronic laboratory notebook database using the execution data.

3. The method of claim 1, further comprising:
receiving variant data that relates to at least one step of the sequence of unit operations specified by the recipe; and
generating the worksheet representing laboratory effects of performing the at least one step in accordance with the variant data.

4. The method of claim 1, further comprising:
receiving an indication that a final step of the first unit operation has been concluded;
in response, automatically initiating a first step of a second unit operation.

5. The method of claim 1, wherein automatically populating execution data of the second worksheet comprises:
obtaining data readings from one or more laboratory equipment systems; and
populating fields in the second worksheet corresponding to the obtained data readings.

6. The method of claim 1, wherein automatically populating bioprocess data comprises:
obtaining data from a database that stores up-to-date information about a state of a laboratory; and
populating fields in the second worksheet corresponding to the obtained data.

7. The method of claim 6, wherein the data represents up-to-date inventory information about one or more input materials to the bioprocess.

8. The method of claim 1, wherein automatically populating the execution data comprises:
obtaining output data for the particular step of the first unit operation; and
populating the second worksheet with the output data.

9. The method of claim 1, wherein the execution data comprises container transfer information representing substances transferred from one container to another.

10. The method of claim 1, wherein the electronic laboratory notebook object is compatible with one or more other electronic laboratory notebook systems.

11. The method of claim 10, wherein the electronic laboratory notebook object is accessed using the one or more other electronic laboratory notebook systems.

12. The method of claim 10, wherein the corresponding worksheet interface for displaying bioprocess data and receiving execution data is rendered on a user device that does not have access to the underlying electronic laboratory notebook database.

13. The method of claim 1, further comprising:
receiving, through a user-interface comprising a set of unit operation objects and one or more links for connecting unit operation objects, the sequence of unit operations specified by the recipe representing the bioprocess through an arrangement of the unit operations into an order using the one or more links;
receiving corresponding data comprising one or more of material inputs, material outputs, bioprocess parameters, equipment, and steps for each unit operation object; and
storing each of the unit operations in the sequence of unit operations specified by the recipe representing the bioprocess and the corresponding data in the electronic laboratory notebook database.

14. The method of claim 1, wherein the worksheet interface for displaying bioprocess data and receiving execution data comprises:
a steps panel comprising a set of tabs, wherein each tab represents a step in the unit operation, and wherein a particular tab is highlighted as a particular step selected from the unit operation;
a notebook panel corresponding with the selected step, wherein the notebook panel is juxtaposed with the steps panel, and the notebook panel includes:
a text display portion comprising instructions for the step,
a table display portion comprising one or more of a material inputs table, a bioprocess parameter table, or an equipment table for displaying data pertaining to performing the step from the corresponding electronic laboratory notebook object and receiving execution data pertaining to the execution of the step by a user,
an assay display portion comprising a representation of contents of one or more wells of an assay plate, or
a results display portion for receiving and displaying results.

15. The method of claim 14, wherein the text display portion further comprises rich-formatted instructions for the step.

16. The method of claim 1, further comprising:
in response to a user request, accessing a particular laboratory notebook object using the electronic laboratory notebook database; and providing the particular laboratory notebook object for display on a user device.

17. The method of claim 16, further comprising receiving an indication of validation for the particular laboratory notebook object from the user device.

18. The method of claim 1, wherein receiving execution data entered into the worksheet interface for a particular step of a first unit operation comprises:
- receiving execution data from a first user device displaying the worksheet interface; and
- receiving execution data from a second user device displaying the worksheet interface.

19. A distributed laboratory execution platform system comprising a plurality of computers maintaining an electronic laboratory notebook database and one or more storage devices storing instructions that are operable, when executed by the one or more computers, to cause the one or more computers to perform operations comprising:
- receiving, by the distributed laboratory execution platform system, a request to execute a sequence of unit operations specified by a recipe representing a bioprocess, wherein each unit operation defines one or more steps to be performed;
- generating, for each step of each unit operation, a worksheet for each step of each unit operation representing laboratory effects of performing the step and having a worksheet interface for displaying bioprocess data and receiving execution data, including initializing, for each worksheet, a corresponding electronic laboratory notebook object in the electronic laboratory notebook database, wherein each corresponding electronic laboratory notebook object is generated from a step of a particular stored unit operation and is associated with the particular stored unit operation by the electronic laboratory notebook database;
- receiving, by the plurality of computers in the distributed lab execution platform system, execution data entered into the worksheet interface for a particular step of a first unit operation;
- updating, in the electronic laboratory notebook database, the corresponding electronic laboratory notebook object using the execution data; and
- in response to receiving an indication that a next step of the first unit operation has been initiated, automatically populating one or more of bioprocess data or execution data of a second worksheet corresponding to the next step of the first unit operation using the electronic laboratory notebook database.

* * * * *